(12) United States Patent
Hall, Jr. et al.

(10) Patent No.: US 9,335,274 B2
(45) Date of Patent: May 10, 2016

(54) OPTICAL INSPECTION OF CONTAINERS

(75) Inventors: George H. Hall, Jr., Toledo, OH (US);
Benjamin L. Daniel, Gibsonburg, OH (US); Stephen M. Graff, Maumee, OH (US); John W. Juvinall, Ottawa Lake, MI (US); Timothy A. Kohler, Waterville, OH (US); Thomas F. Michalski, Maumee, OH (US); James A. Ringlien, Maumee, OH (US)

(73) Assignee: Owens-Brockway Glass Container Inc., Perrysburg, OH (US)

( * ) Notice: Subject to any disclaimer, the term of this patent is extended or adjusted under 35 U.S.C. 154(b) by 342 days.

(21) Appl. No.: 13/172,258

(22) Filed: Jun. 29, 2011

(65) Prior Publication Data

US 2013/0002851 A1 Jan. 3, 2013

(51) Int. Cl.
*G01N 21/90* (2006.01)

(52) U.S. Cl.
CPC ............ *G01N 21/90* (2013.01); *G01N 21/9018* (2013.01); *G01N 21/9054* (2013.01)

(58) Field of Classification Search
None
See application file for complete search history.

(56) References Cited

U.S. PATENT DOCUMENTS

| | | | |
|---|---|---|---|
| 4,335,960 A | | 6/1982 | Ashcroft et al. |
| 4,959,537 A | * | 9/1990 | Kimoto et al. ............ 250/223 B |
| 5,461,228 A | | 10/1995 | Kirkman et al. |
| 6,031,221 A | | 2/2000 | Furnas |
| 6,072,575 A | | 6/2000 | Löll |
| 6,175,107 B1 | | 1/2001 | Juvinall |
| 6,198,102 B1 | | 3/2001 | Shepherd |
| 7,414,716 B2 | | 8/2008 | Sones et al. |
| 7,477,374 B2 | | 1/2009 | Schmidt et al. |
| 7,541,572 B2 | | 6/2009 | Novini et al. |
| 2004/0223342 A1 | * | 11/2004 | Klipstein et al. .............. 362/555 |
| 2005/0219523 A1 | * | 10/2005 | Onuma et al. ............. 356/239.5 |
| 2006/0140470 A1 | * | 6/2006 | Watanabe ..................... 382/142 |
| 2006/0180775 A1 | * | 8/2006 | Paradis .................... 250/559.42 |
| 2010/0194878 A1 | * | 8/2010 | Sones et al. ................... 348/127 |
| 2010/0225908 A1 | * | 9/2010 | Kwirandt ................... 356/239.4 |

FOREIGN PATENT DOCUMENTS

EP   1 494 013 A1   6/2004

OTHER PUBLICATIONS

International Search Report and Written Opinion of the International Searching Authority, International Application No. PCT/US2012/041074, International Filing Date: Jun. 6, 2012, Date of Mailing: Sep. 3, 2012; 11 pages.

* cited by examiner

*Primary Examiner* — Mehrdad Dastouri
*Assistant Examiner* — James M Anderson, II

(57) ABSTRACT

An apparatus and method for inspecting a container having a base and a mouth, wherein light is directed through the container base into the container, and out of the container through the container mouth, using at least first and second light sources operatively disposed adjacent to each other beneath the container base and having differing operating characteristics. Light transmitted through the container mouth is sensed, and a composite image of the container mouth may be produced from two or more images of portions of the container mouth.

28 Claims, 6 Drawing Sheets

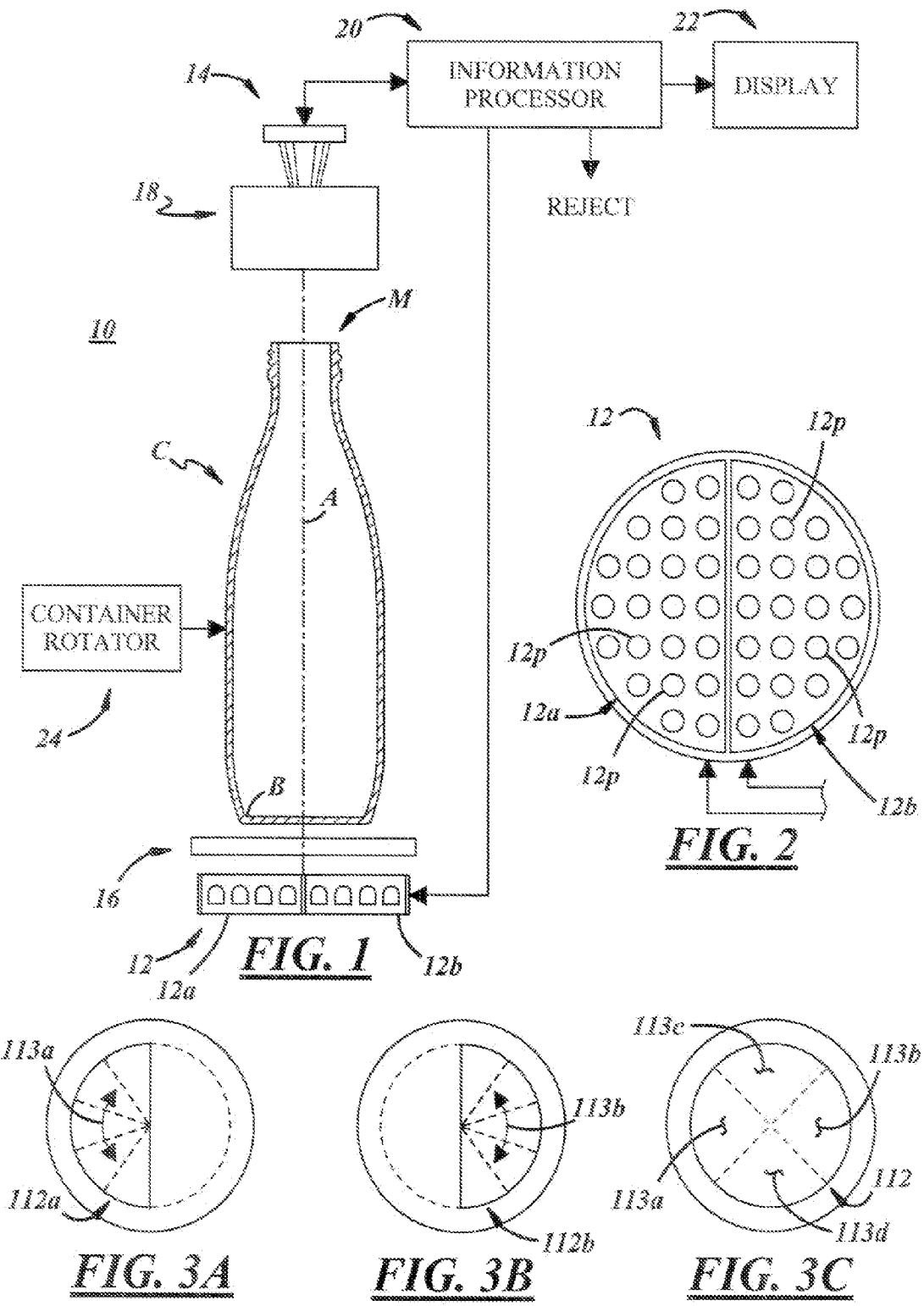

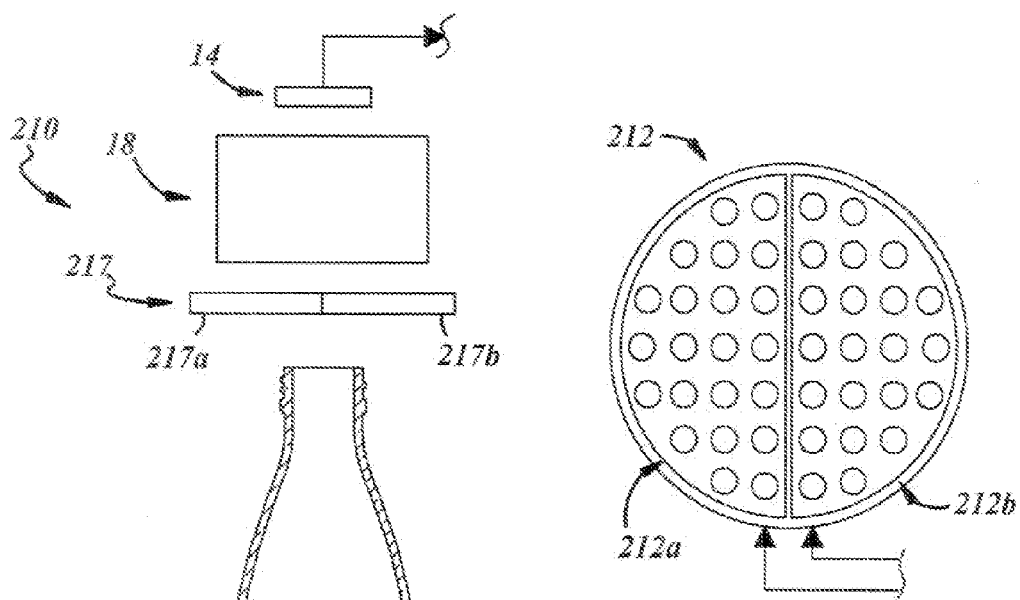
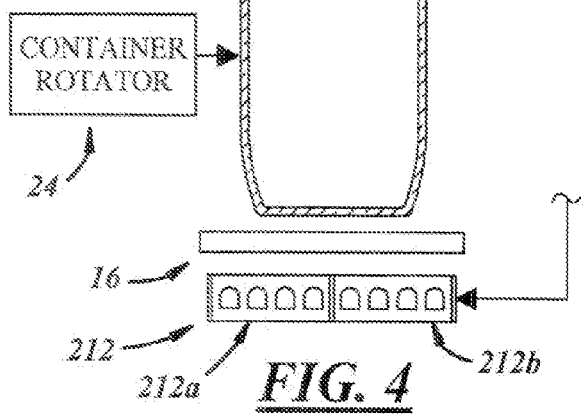
FIG. 5
FIG. 4
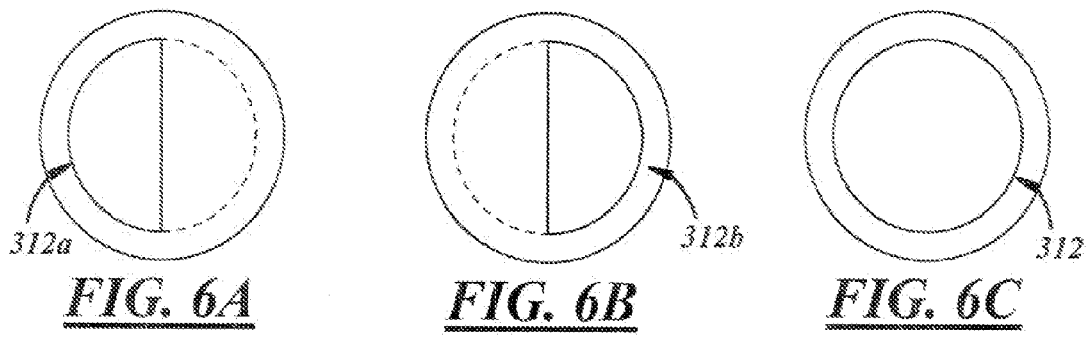
FIG. 6A  FIG. 6B  FIG. 6C

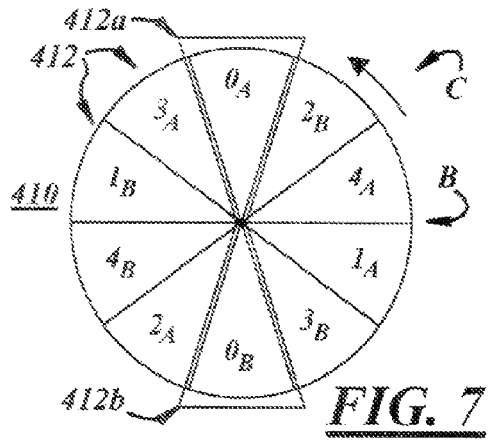
*FIG. 7*
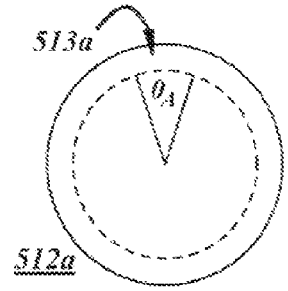
*FIG. 8A*
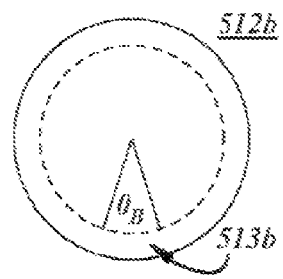
*FIG. 8B*
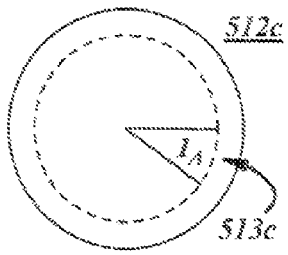
*FIG. 9A*
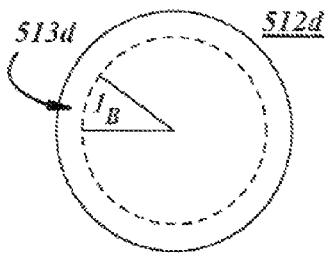
*FIG. 9B*
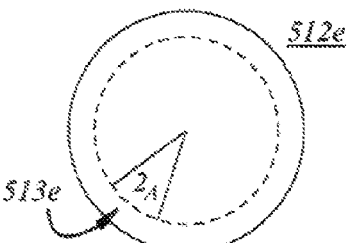
*FIG. 10A*
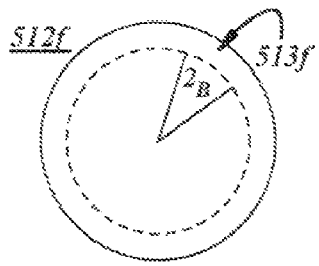
*FIG. 10B*
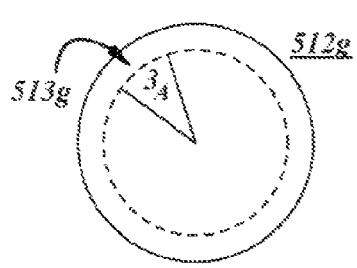
*FIG. 11A*
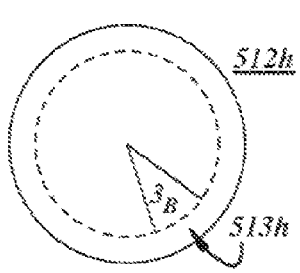
*FIG. 11B*
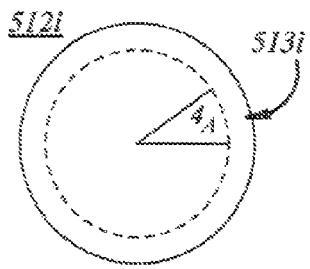
*FIG. 12A*
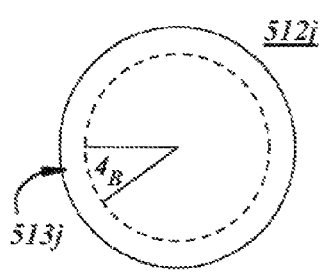
*FIG. 12B*
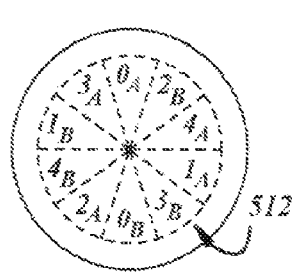
*FIG. 13*

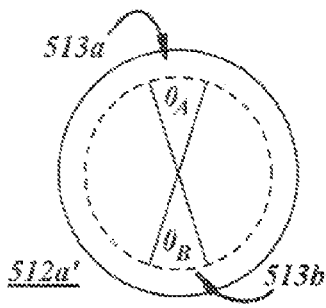
*FIG. 8*
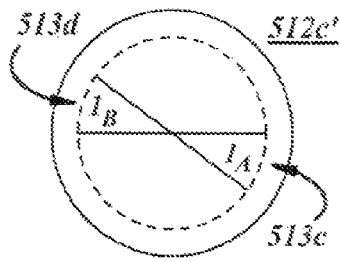
*FIG. 9*
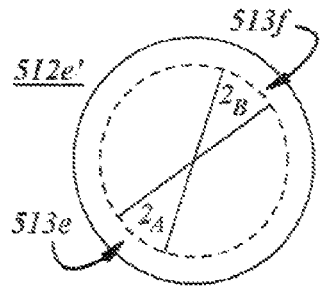
*FIG. 10*
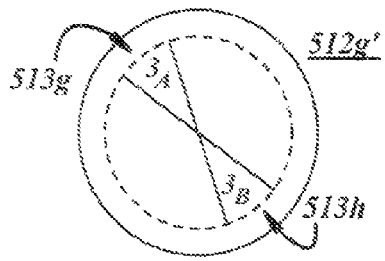
*FIG. 11*
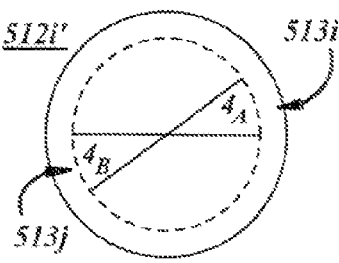
*FIG. 12*
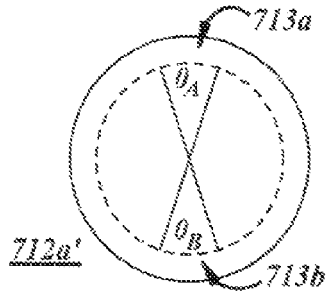
*FIG. 15*
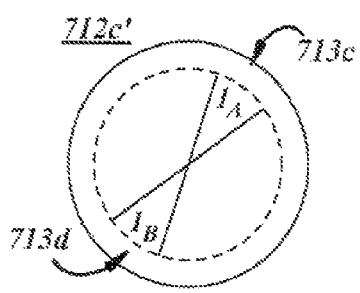
*FIG. 16*
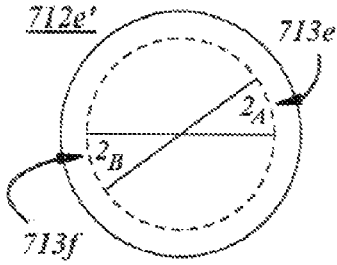
*FIG. 17*
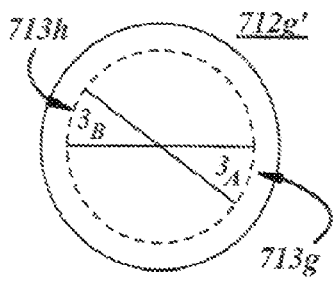
*FIG. 18*
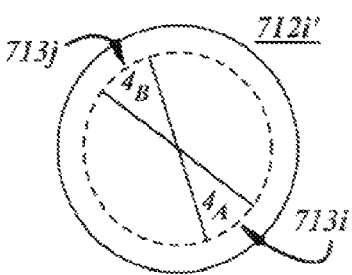
*FIG. 19*

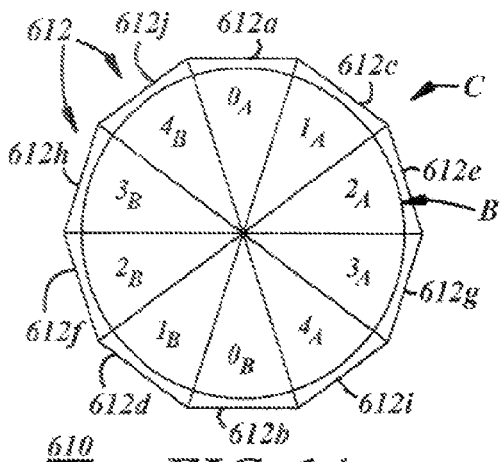
FIG. 14
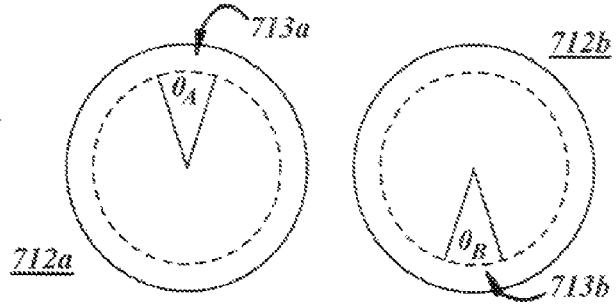
FIG. 15A    FIG. 15B
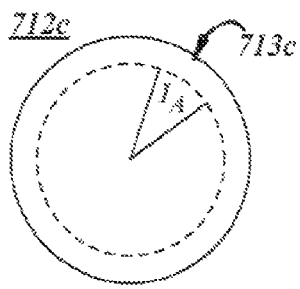 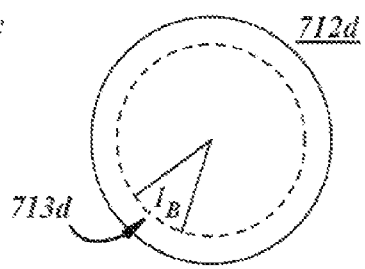 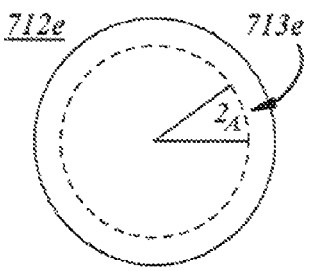
FIG. 16A    FIG. 16B    FIG. 17A
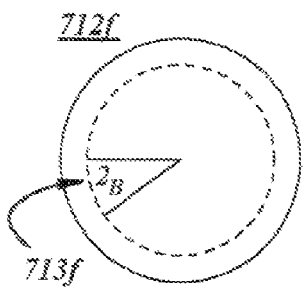 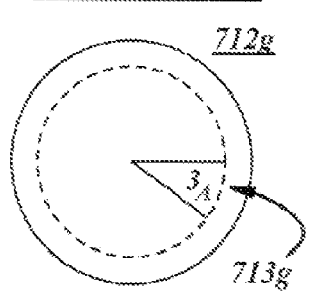 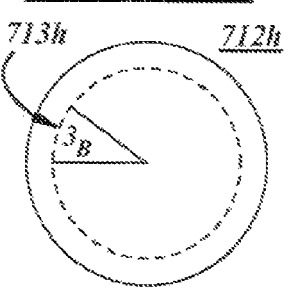
FIG. 17B    FIG. 18A    FIG. 18B
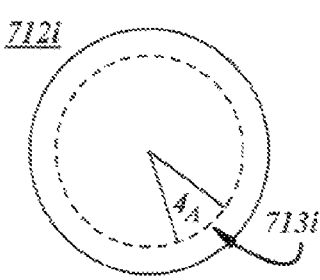 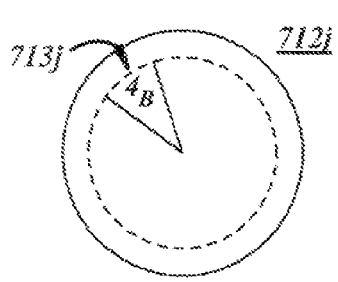 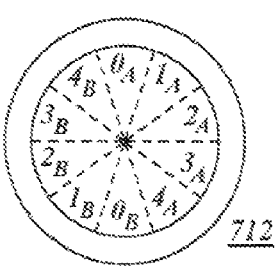
FIG. 19A    FIG. 19B    FIG. 20

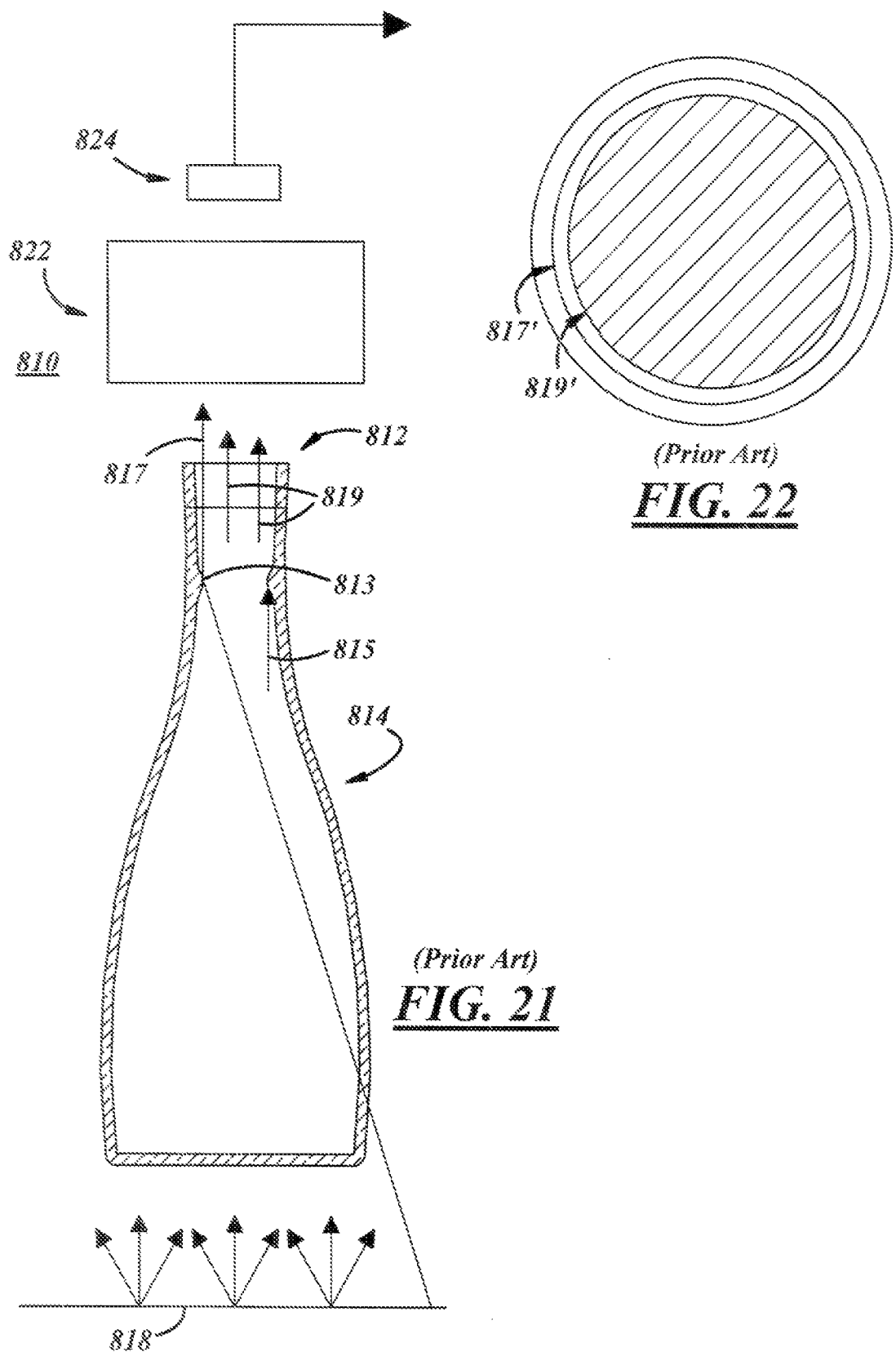
(Prior Art)
FIG. 21
(Prior Art)
FIG. 22

OPTICAL INSPECTION OF CONTAINERS

The present disclosure is directed to methods and apparatus for optical inspection of containers.

BACKGROUND AND SUMMARY OF THE DISCLOSURE

In the manufacture of containers, various anomalies or variations can occur that affect the commercial acceptability of the containers. These anomalies, termed "commercial variations," can involve one of numerous attributes of the container. For example, commercial variations can include dimensional characteristics of the container at an open mouth of the container. Thus, it is often times useful to provide inspection equipment capable of inspecting the containers for commercial variations. The term "inspection" is used in its broadest sense to encompass any optical, electro-optical, mechanical or electrical observation or engagement with a container to measure or determine a potentially variable characteristic, including but not necessarily limited to commercial variations.

FIG. 21 illustrates in simplified and diagrammatic form an apparatus 810 for inspecting parameters of a container mouth 812 in one type of inspection process for a container 814 that generally conforms to an apparatus shown and described in U.S. Pat. No. 5,461,228, which is assigned to the assignee hereof and is incorporated herein by reference. The apparatus 810 includes a light source 818 that directs light into the container 814, and a light sensor 824 disposed with respect to the light source 818 and the container 814 to receive light transmitted out of the container 814 through the container mouth 812. A telecentric lens 822 directs onto the light sensor 824 only light transmitted through the container mouth 812 substantially axially of the container mouth 812. The sensor 824 develops a two-dimensional image of the container mouth 812. The sensor 812 is coupled to image processing electronics (not shown) for determining or calculating a circle of greatest diameter that will fit within the two-dimensional image of the container mouth 812, and treating such circle as indicative of the effective inside diameter of the container mouth 812.

The container 814 may include commercial variations like choke portions 813 that may block some light rays 815 and reflect other, angled, light rays 817 in a direction generally parallel with the container longitudinal axis. The sensor 824 senses not only unimpeded light rays 819 that indicate the inside diameter of the container mouth 812, but also the reflected light rays 817, which tend to make the container mouth 812 appear larger than it really is. Accordingly, as shown in prior art FIG. 22, a prior art light image produced by light from the light source of FIG. 21 includes a pattern of bright unimpeded light 819' representing the inside diameter of the mouth 812 and a halo or additional pattern of reflected light 817' representing the reflections off the inside diameter of the mouth 812.

A general object of the present disclosure, in accordance with one aspect of the disclosure, is to provide a more reliable optical plug gage (OPG) apparatus for gaging a container mouth to reduce or eliminate reflected light in an OPG image, and/or to prevent passage of certain light rays reflected from an inside surface of a container mouth in a direction parallel to a container axis to a light sensor so that the container mouth does not appear larger than actual size.

The present disclosure embodies a number of aspects that can be implemented separately from or in combination with each other.

An apparatus for inspecting a container having a base and a mouth in accordance with one aspect of the disclosure includes a light source for directing light through the container base into the container, and out of the container through the container mouth. The apparatus also includes a light sensor disposed with respect to the light source and the container to receive light transmitted through the container mouth. The light source includes at least first and second light sources operatively disposed adjacent to each other beneath the container base and having differing operating characteristics.

In accordance with another aspect of the disclosure, there is provided a method of inspecting a container having a base and a mouth, including the step of directing light through the container base into the container, and out of the container through the container mouth, using at least first and second light sources operatively disposed adjacent to each other beneath the container base and having differing operating characteristics. The method also includes the step of sensing light transmitted through the container mouth.

BRIEF DESCRIPTION OF THE DRAWINGS

The disclosure, together with additional objects, features, advantages and aspects thereof, will be best understood from the following description, the appended claims and the accompanying drawings, in which:

FIG. 1 is a schematic diagram of an optical plug gage apparatus for evaluating a mouth of a container in accordance with an exemplary embodiment of the present disclosure, and including a light source;

FIG. 2 is a schematic top view of the light source of FIG. 1;

FIGS. 3A-3C are schematic views of light images produced by light captured by a light sensor and emanating from the light source of FIG. 1 through the container mouth of FIG. 1;

FIG. 4 is a schematic diagram of an optical plug gage apparatus for evaluating a mouth of a container in accordance with another exemplary embodiment of the present disclosure, and including a light source;

FIG. 5 is a schematic top view of the light source of FIG. 4;

FIGS. 6A-6C are schematic views of light images produced by light captured by a light sensor and emanating from the light source of FIG. 4 through the container mouth of FIG. 4;

FIG. 7 is a schematic diagram of a portion of another optical plug gage apparatus for evaluating a mouth of a container in accordance with another exemplary embodiment of the present disclosure, and including a light source;

FIGS. 8A-12B are schematic views of light images produced by light captured by a light sensor and emanating in a sequential manner from the light source(s) of FIG. 7 through the container mouth of FIG. 4;

FIGS. 8-12 are schematic views of light images produced by light captured by a light sensor and emanating in a simultaneous manner from the light source(s) of FIG. 7 through the container mouth of FIG. 4;

FIG. 13 is a schematic view of a composite light image of the light images of FIGS. 8A-12B;

FIG. 14 is a schematic diagram of a portion of an additional optical plug gage apparatus for evaluating a mouth of a container in accordance with another exemplary embodiment of the present disclosure, and including a light source;

FIGS. 15-19 are schematic views of light images produced by light captured by a light sensor and emanating in a simultaneous manner from the light source(s) of FIG. 7 through the container mouth of FIG. 4;

FIGS. 15A-19B are schematic views of light images produced by light captured by a light sensor and emanating from the light source(s) of FIG. 14 through the container mouth of FIG. 4;

FIG. 20 is a schematic view of a composite light image of the light images of FIGS. 15A-19B;

FIG. 21 is a schematic diagram of an optical plug gage apparatus for evaluating a mouth of a container in accordance with the prior art; and FIG. 22 is a schematic view of a prior art light image produced by light captured from a light sensor and emanating from a light source of FIG. 21 through the container mouth of FIG. 21

DETAILED DESCRIPTION OF PREFERRED EMBODIMENTS

FIG. 1 illustrates an exemplary embodiment of an optical plug gage apparatus 10 for inspecting an open mouth M of a container C. The apparatus 10 includes one or more light sources 12 operatively disposed below the container C to produce light used in inspecting the container mouth M, and one or more light sensors 14 disposed above the container C to sense light produced by the light source 12 and passing through the container mouth M. As used herein, the terminology "operatively disposed" includes light sources that may be located anywhere but emit light from below the container C, for example, via mirrors, fiber optics or the like. The apparatus 10 optionally may include one or more light diffusers 16 disposed between the light source 12 and the container C to diffuse and/or direct light through a bottom B of the container C into the container C and through the container mouth M. The apparatus 10 further may include a lens system 18 disposed between the container C and the light sensor 14 to direct light passing through the container mouth M to the light sensor 14. The apparatus 10 additionally may include a processor 20 or any other suitable device(s) to scan the light sensor 14 and develop an image of the container mouth M and/or any other suitable inspection information, and a display 22 to display the image and/or other inspection information. The apparatus 10 also may include a container rotator 24 to rotate the container C.

The container C may be a jar, or a bottle as illustrated in FIG. 1, or any other suitable type of container. The container C may be composed of plastic, glass, or any other suitable material. The container C may be clear, colored, transparent, translucent, or of any other suitable optical quality.

Referring to FIGS. 1 and 2, the light source 12 may include a plurality of light sources 12a, 12b, each of which may include one or more discrete light elements 12p (FIG. 2). For example, the light source 12 may include at least two light sources 12a, 12b that may be diametrically opposed to one another and/or operatively disposed adjacent to each other beneath the container base B (FIG. 1), and that may be energized independently and alternatingly. In another example, the light elements 12p (FIG. 2) may include a plurality of light emitting diodes (LEDs), wherein the light source 12 may be a multiple-LED light source. In any case, those of ordinary skill in the art will recognize that the light source 12 may receive power from any suitable source in any suitable manner and may be controlled by the processor 20 (FIG. 1) in any suitable manner. Moreover, those of ordinary skill in the art will recognize that the light source 12 may be divided into sub-sections or sub-portions or may be composed of two separate light sources.

The plurality of light sources 12a, 12b may have differing operating characteristics. In one example embodiment, the light sources 12a, 12b may be energized alternatingly or sequentially, for example, with no overlap in emission of light. In another example embodiment, the light sources 12a, 12b may emit light of different wavelengths with simultaneous emission of light. The example different operating characteristics will be described below in greater detail.

With reference to FIG. 1, the light sensor 14 may include any suitable device to sense light. For example, the light sensor 14 may include an image sensor, for instance, a charge-coupled device (CCD), complementary metal-oxide-semiconductor (CMOS) device, or any other suitable image sensor. In another example, the light sensor 14 may include a photodiode device, a photoresistor device, or any other suitable photodetector device.

The light diffuser 16 may include any suitable device to diffuse light. For example, the light diffuser 16 may include a ground glass diffuser, a teflon diffuser, a holographic diffuser, an opal glass diffuser, a greyed glass diffuser, or any other suitable diffuser.

The lens system 18 may include any suitable device to direct or focus light. For example, the lens system 18 may include a telecentric lens, an entrance pupil, and pupil lenses on either side of the pupil. The lens system 18 may direct only light rays that emerge from the container mouth M essentially parallel to an axis A of the container C.

The processor 20 may include any suitable device(s) to acquire images from the light sensor 14 and output images to the display 22. The container rotator 24 may include any suitable device to rotate the container C.

For example, the rotator 24 may include one or more rollers, wheels, belts, discs, and/or any other suitable element(s) to rotate the container C. In another embodiment, the container C may remain stationary, and one or more of the various apparatus elements 12, 14, 16, 18 may be rotated in any suitable manner.

In one example of operation, the first light source 12a is energized, and light from that first light source 12a extending parallel to the container axis A and through the container mouth M is sensed by the light sensor 14 to obtain a corresponding first image 112a as shown in FIG. 3A. Any reflections that may impinge on the right half of the sensor 14 may be digitally discarded, for example, by the information processor 20. Then, the first light source 12a is de-energized and the second light source 12b is energized and light from that second light source 12b extending parallel to the container axis A and through the container mouth M is sensed by the light sensor 14 to obtain a corresponding second image 112b as shown in FIG. 3B. Any reflections that may impinge on the left half of the sensor 14 may be digitally discarded, for example, by the information processor 20.

In one embodiment, images of the container mouth M may be acquired in pairs. The first image 112a of the pair is acquired by the light sensor 14, and transfer of the image 112a from the light sensor 14 to the processor 20 is begun, then a short time (e.g. sub-millisecond) elapses, and thereafter the second image 112b of the pair is acquired while the first image 112a is still being transferred. Accordingly, the images 112a, 112b are obtained selectively, sequentially, and synchronously.

Although each of the images 112a, 112b include approximately 180 circumferentially angular degrees of the container mouth M, only select portions, for example central portions 113a, 113b, of the images 112a, 112b can be assumed to be essentially free of low-angle reflections that would interfere with image processing. This is because regions of the container mouth M that are coincident with the divider of the light source 12 (or edges of the light sources 12a, 12b) could have some low-angle reflections. Accordingly, only the central portions 113a, 113b of the images 112a, 112b may be evaluated.

An example circumferentially angular range of the central portions 113a, 113b may be 30 to 120 circumferentially angular degrees as depicted in FIGS. 3A and 3B. Stated another way, an example circumferentially angular range of the central portions 113a, 113b may be about 15% to about 70% of the circumferentially angular extent of the corresponding 112a, 112b images. In one specific example, the central portions 113a, 113b each may be 90 circumferentially angular degrees, to result in corresponding portions 113a, 113b in a composite image 112. Therefore, it may be desirable to capture similar, additional, angularly interposed and adjacent image portions 113c, 113d in the composite image 112. This may be accomplished by rotating the container C, for example, 90 circumferentially angular degrees, and capturing the other pair of images 113c, 113d of portions of the container mouth M in the manner described above. Accordingly, the composite image 112 may include a full 360 circumferentially angular degrees of the container mouth M. This may be particularly desirable for inspection of commercial variations or where a circumferentially continuous diametric measurement of the container mouth M. Those of ordinary skill in the art will recognize that more image portions may be obtained and evaluated, for example, twelve 30-degree portions, ten 36-degree portions, six 60-degree portions, and/or the like.

As shown in FIG. 3C, the first and second images 112a, 112b can be superimposed or added to obtain a complete image 112 of the inside of the container mouth M. The image 112 can be used to identify commercial variations in the container, measure the inside diameter of the container mouth M, or for any other suitable container inspection techniques.

According to the present disclosure, stray light (exemplified by numerals 817, 817' in FIGS. 21 and 22) that is reflected by a choke or other portions of the container C along a direction generally parallel to the container axis A will be ignored, one way or another. For example, in the above-described embodiment, when the right side or section light source 12b is activated and the corresponding image portion 112b (FIG. 3B) is sampled or acquired, reflected light (as exemplified by numeral 817 on the left side in FIG. 21) that emerges from the right side or section light source 12b is ignored because it impinges on the left side of the image sensor 14 and the corresponding image portion 112a is ignored. In other words, because low-angle light reflections typically originate from a side of the light source 12 opposite that of the reflecting surface of the container C, the reflections are largely eliminated by not evaluating that portion of the container mouth M opposite of the energized light source 12b.

FIG. 4 illustrates another exemplary embodiment of an optical plug gage apparatus 210 for inspecting a mouth M of a container C. This embodiment is similar in many respects to the embodiment of FIG. 1 and like numerals between the embodiments generally designate like or corresponding elements throughout the several views of the drawing figures. Accordingly, the descriptions of the embodiments are incorporated into one another. Additionally, the description of the common subject matter generally may not be repeated here.

A light source 212 may have a plurality of light sources 212a, 212b that produce light of differing wavelengths. For example, the light source 212 may be a multiple-LED type of light source with differing wavelength LEDs of the respective light sources 212a, 212b. In a more specific example, shorter-wavelength LEDs may be provided on a first light source 212a and longer-wavelength LEDs may be provided on a second light source 212b. For instance, and by way of example only, the shorter-wavelength LEDs may emit light at 740 nm wavelength, and the longer wavelength LEDs may emit light at 850 nm.

A filter 217 is positioned between the container C and the light sensor 14. The filter 217 may include a plurality of filters 217a, 217b that filter light of differing wavelengths. For example, a first filter 217a may be a short pass filter to filter out longer wavelength light emanating from the second light source 212b and allow passage of shorter wavelength light emanating from the second light source 212b. In another example, a second filter 217b may be a long pass filter to filter out shorter wavelength light emanating from the first light source 212a and allow passage of longer wavelength light emanating from the first light source 212a. The short pass filter 217a on the left side will not admit stray light from the right side of the light source 212b that gets reflected from a choke in the container neck, and vice versa. Moreover, those of ordinary skill in the art will recognize that the filter 217 may be divided into sub-sections or may be composed of two separate filters.

In one example of operation, both sides of the light source 212 can be energized simultaneously. Accordingly, light from both the first and second light sources 212a, 212b extending parallel to the container axis A and through the container mouth M is sensed by the light sensor 14 to obtain corresponding first and second images 312a, 312b as shown in FIGS. 6A and 6B. Accordingly, the images 312a, 312b are obtained simultaneously to produce one image 312 of the container mouth M. Like the previous embodiment, less than the entirety of each image 312a, 312b may be evaluated and, thus, the container C may be rotated to obtain additional interposed images.

According to the present disclosure, stray light (exemplified by numerals 817, 817' in FIGS. 21 and 22) that is reflected by a choke or other portions of the container C along a direction generally parallel to the container axis A will be ignored, one way or another. For example, in the embodiment of FIGS. 4 through 6C, the reflected light as exemplified on the left side in FIG. 21 is ignored because it emerges from the longer-wavelength second light source 212b but is blocked by the shorter wavelength filter 217a.

FIG. 7 illustrates another exemplary embodiment of a portion of an optical plug gage apparatus 410, wherein a container may be inspected as it rotates about its longitudinal axis. This embodiment is similar in many respects to the embodiments of FIGS. 1-6C and like numerals between the embodiments generally designate like or corresponding elements throughout the several views of the drawing figures. Accordingly, the descriptions of the embodiments are incorporated into one another. Additionally, the description of the common subject matter generally may not be repeated here.

The apparatus 410 includes one or more light sources 412 operatively disposed below the base B of the container C to produce light used in inspecting the container mouth (not shown). In one example of this embodiment, the light sources 412 may include a pair of light sources 412a, 412b, that may be diametrically opposed to one another. Each of the light sources 412a, 412b may correspond to portions or segments of the container base B. For example, each light source 412a, 412b may be about 1/X in circumferentially angular size, wherein the container base B theoretically may be divided into X segments and wherein X is a quantity of images to be captured of the container. More specifically, the container base B may be divided into 2, 4, 6, or 8 equal segments, or, as shown, 10 equal segments, or any other suitable number of segments. Accordingly, in the illustrated example, each light source of the light sources 412a, 412b may be about thirty six degrees in circumferentially angular size and the quantity of images equals ten. As used herein, the phrase "about 1/X" may include within plus or minus ten degrees. Therefore, for example, each light source 412a, 412b may be about forty degrees in circumferentially angular size with a quantity of images still equal to ten such that there is some circumferential overlap in images produced from the light sources 412a, 412b. The overlap may be included, for example, to address slippage between the container rotator and the container, variable latencies in image frame acquisition, errors in rotation encoding, and/or the like.

In a first example of operation, the container C may be inspected as it rotates, and this example corresponds to the embodiment of FIGS. 1 through 3C. Upon arrival of the container C at an inspection station of the apparatus 410, the container C may be stationary, may begin to rotate, or may be rotating already. Also, upon arrival, and referring to FIG. 7, the portions 412a, 412b of the light source 412 are energized alternately or sequentially and light from that source is sensed by the light sensor to sequentially obtain the corresponding first and second images 512a, 512b and select portions 513a, 513b thereof as shown in FIGS. 8A and 8B. More specifically, the first light source 412a is energized, and light from that first light source 412a extends through a corresponding segment $0_A$ of the container base B parallel to the container axis and through the container mouth M. That light is sensed by a light sensor to obtain a corresponding first image 512a and a select portion 513a thereof as shown in FIG. 8A. Then, the first light source 412a is de-energized and the second light source 412b is energized, and light from that second light source 412b extends through another corresponding segment $0_B$ diametrically opposed to the first segment $0_A$ parallel to the container axis and through the container mouth. That light is sensed by the light sensor to obtain a corresponding second image 512b and a select portion 513b as shown in FIG. 8B.

Because the time of rotation of the container C may be faster than the time required for the image sensor to process the images, the container C may have circumferentially indexed over some circumferentially angular range before additional imaging occurs. For example, by the time the image sensor is ready to process additional images, segment $1_A$ of the container base B will be aligned in correspondence with the light source 412a and opposed segment $1_B$ of the container base B will be aligned in correspondence with the light source 412b. In a more specific example, at an initial time (0 milliseconds) when the light sources 412a, 412b are sequentially energized to illuminate the container base B, the angular rotation of the container C at that instant is considered zero. But, by the time the image sensor is ready to process additional images, for example about 16.4 milliseconds later, the container C will have rotated nearly 3/10 of a full rotation. Accordingly, subsequent imaging may be activated, for example, about 20 milliseconds after the previous imaging and such imaging corresponds to segments $1_A$, $1_B$ of the container base B.

At that instant, the first light source 412a is again energized, and light from that first light source 412a extends through the corresponding segment $1_A$ of the container base B parallel to the container axis and through the container mouth. That light is sensed by the light sensor to obtain a corresponding third image 512c and a select portion 513c thereof as shown in FIG. 9A. Then, the first light source 412a is de-energized and the second light source 412b is energized, and light from that second light source 412b extends through another corresponding segment $1_B$ diametrically opposed to the first segment $1_A$ parallel to the container axis and through the container mouth. That light is sensed by the light sensor to obtain a corresponding fourth image 512d and a select portion 513d thereof as shown in FIG. 9B.

This operation repeats until the container C has rotated 12/10 (twelve-tenths) of a full revolution and wherein fifth through tenth images 512e through 512j and selection portions 513e through 513j thereof are obtained corresponding to container base segments 2A through 4B, as shown in FIGS. 10A through 12B. Before a subsequent container arrives at the station to be inspected, the container C may rotate beyond 12/10 of the full revolution, for example, about 1.5 revolutions. The operation may occur, for example, over about 80 milliseconds; the time for five pairs of images to be processed and including the time for circumferential indexing of the container C therebetween.

In a second example of operation, the container C may be inspected as it rotates, and this example corresponds to the embodiment of FIGS. 4 through 6C. Upon arrival of the container C at an inspection station of the apparatus 410, the container C may be stationary, may begin to rotate, or may be rotating already. Also, upon arrival, both light sources 412a, 412b are energized simultaneously. Accordingly, light from both the first and second light sources 412a, 412b extend through corresponding theoretical segments $0_A$, $0_B$ of the container base B parallel to the container axis, through the container mouth, and through the filter 217 (FIG. 4). That light is sensed by the light sensor to simultaneously obtain a corresponding first image 512a' and select portions 513a, 513b thereof as shown in FIG. 8.

Again, because the time of rotation of the container C may be faster than the time required for the image sensor to process the images, the container C may have circumferentially indexed over some circumferentially angular range before additional imaging occurs. For example, by the time the image sensor is ready to process additional images, segment $1_A$ of the container base B will be aligned in correspondence with the light source 412a and opposed segment $1_B$ of the container base B will be aligned in correspondence with the light source 412b. At that instant, both light sources 412a, 412b are energized simultaneously. Accordingly, light from both the first and second light sources 412a, 412b extend through corresponding theoretical segments $1_A$, $1_B$ of the container base B parallel to the container axis and through the container mouth. That light is sensed by the light sensor to obtain a corresponding second image 512c' and select portions thereof 513c, 513d as shown in FIG. 9. This operation repeats until third through fifth images 512e' through 512i' and select portions thereof 513e through 513j are also obtained corresponding to container base segments $2_A$ through $4_B$, as shown in FIGS. 10 through 12.

In one or both of the aforementioned operational examples, the images 512a' through 512i' and the select portions 513a through 513j may be summed in any suitable manner to produce one image 512 of the container mouth M, as shown in FIG. 13. That image 512 then may be inspected according to any suitable inspection techniques for size, shape, anomalies, or the like.

FIG. 14 illustrates another exemplary embodiment of a portion of an optical plug gage apparatus 610, wherein a container may be inspected as it is circumferentially stationary. This embodiment is similar in many respects to the embodiments of FIGS. 1-13 and like numerals between the embodiments generally designate like or corresponding elements throughout the several views of the drawing figures. Accordingly, the descriptions of the embodiments are incorporated into one another. Additionally, the description of the common subject matter generally may not be repeated here.

The apparatus 610 includes one or more light sources 612 operatively disposed below the base B of the container C to produce light used in inspecting the container mouth (not shown). The light sources 612 may include a plurality of pairs of light sources 612a through 612j, each pair of which may include two diametrically opposed sources. Each of the light sources 612a through 612j may correspond to portions or segments of the container base B. For example, each light source 612a through 612j may be about 1/X in circumferentially angular size, wherein the container base B theoretically may be divided into X segments and wherein X is a quantity of images to be captured of the container. More specifically, the container base B may be divided into 2, 4, 6, or 8 equal segments, or, as shown, 10 equal segments, or any other suitable number of segments. Accordingly, in the illustrated example, each light source of the plurality of pairs of light sources 612a through 612j is about thirty six degrees in circumferentially angular size and the quantity of images equals ten.

In this embodiment, the container C is not rotated or is stationary as the plurality of pairs of light sources 612a through 612j are energized circumferentially sequentially around the container C.

In a first example of operation, the container C may be inspected in a circumferentially stationary position, and this example corresponds to the embodiment of FIGS. 1 through 3C. Upon arrival of the container C at an inspection station of the apparatus 610, the container C may be circumferentially stationary.

Also, upon arrival, and referring to FIG. 14, a pair of light sources 612a, 612b are energized alternately or sequentially and light from the sources is sensed by the light sensor to sequentially obtain the corresponding first and second images 712a, 712b and select portions 713a, 713b thereof as shown in FIGS. 15A and 15B. More specifically, a first light source 612a is energized, and light from that first light source 612a extends through a corresponding segment $0_A$ of the container base B parallel to the container axis and through the container mouth. That light is sensed by a light sensor to obtain a corresponding first image 712a and a select portion 713a thereof as shown in FIG. 15A. Then, the first light source 612a is de-energized and a second light source 612b is energized, and light from that second light source 612b extends through another corresponding segment $0_B$ diametrically opposed to the first segment $0_A$ parallel to the container axis and through the container mouth. That light is sensed by the light sensor to obtain a corresponding second image 712b and a select portion 713b as shown in FIG. 15B.

Next, and referring to FIG. 14, a third light source 612c is energized, and light from that third light source 612c extends through a corresponding segment $1_A$ of the container base B parallel to the container axis and through the container mouth. That light is sensed by a light sensor to obtain a corresponding third image 712c and a select portion 713c thereof as shown in FIG. 16A. Then, the third light source 612c is de-energized and a fourth light source 612d is energized, and light from that fourth light source 612d extends through another corresponding segment $1_B$ diametrically opposed to the third segment $1_A$ parallel to the container axis and through the container mouth. That light is sensed by the light sensor to obtain a corresponding fourth image 712d and a select portion 713d as shown in FIG. 16B.

This process continues for additional light sources 612e through 612j to obtain corresponding images 712e through 712j and select portions thereof 713e through 713j, as shown in FIGS. 17A through 19B.

In a second example of operation, the container C may be inspected in a circumferentially stationary position and this example corresponds to the embodiment of FIGS. 4 through 6C. Also, both of a first pair of light sources 612a, 612b are energized simultaneously. Accordingly, light from both the first and second light sources 612a, 612b extend through corresponding theoretical segments $0_A$, $0_B$ of the container base B parallel to the container axis, through the container mouth, and through the filter 217 (FIG. 4). That light is sensed by the light sensor to simultaneously obtain a corresponding first image 712a' and select portions 713a, 713b thereof shown in FIG. 15.

Next, and referring to FIG. 14, a second pair of light sources, for example, third and fourth light sources 612c, 612d, are energized simultaneously, and light from those light sources 612c, 612d extend through corresponding segments $1_A$ and $1_B$ of the container base B parallel to the container axis and through the container mouth. That light is sensed by a light sensor to obtain a corresponding second image 712c' and select portions 713c, 713d thereof shown in FIG. 16.

This process continues for additional light sources 612e through 612j to obtain corresponding images 712e' through 712i' and select portions thereof 713e through 713j, as shown in FIGS. 17 through 19.

In one or both of the aforementioned operational examples, the images 712a through 712j and the select portions 713a through 713j may be summed in an any suitable manner to produce one image 712 of the container mouth M. That image 712 then may be inspected according to any suitable inspection techniques for size, shape, anomalies, or the like.

According to the present disclosure, low-angle reflections are reduced to a degree that does not interfere with image processing because the reflections are at least one of filtered before reaching a light sensor or impinge on a portion of the light sensor that is not presently evaluated.

There thus has been disclosed an apparatus and method for optical inspection of a container, that fully satisfies all of the objects and aims previously set forth. The disclosure has been presented in conjunction with several exemplary embodiments, and additional modifications and variations have been discussed. Other modifications and variations readily will suggest themselves to persons of ordinary skill in the art in view of the foregoing discussion. The disclosure is intended to embrace all such modifications and variations as fall within the spirit and broad scope of the appended claims.

The invention claimed is:

1. An apparatus for inspecting a container having a base and a mouth, said apparatus including:
  a light source for directing light through the container base into the container, and out of the container through the container mouth, and
  a light sensor disposed with respect to said light source and the container to receive light transmitted through the container mouth,
  wherein said light source includes at least first and second light sources operatively disposed adjacent to each other beneath the container base and having differing operating characteristics, and wherein said at least first and second light sources include at least a pair of opposed light sources disposed on opposite sides of a longitudinal axis of the container, and further wherein the differing operating characteristics of the first and second opposed light sources cause different illumination amongst opposed sides of the container mouth disposed on opposite sides of the longitudinal axis of the container, and said light sensor captures images of the container mouth in opposed pairs, each pair of images comprising images of respective segments of the container mouth on opposite sides of the longitudinal axis of the container.

2. The apparatus set forth in claim 1 wherein each of said light sources includes one or more discrete light elements.

3. The apparatus set forth in claim 1, including a light diffuser disposed between said light source and the container.

4. The apparatus set forth in claim 1, including a lens system disposed between the container and said light sensor.

5. The apparatus set forth in claim 1, including a container rotator to rotate the container to different angular positions for capturing additional opposed pairs of images of the container mouth.

6. The apparatus set forth in claim 1 wherein said differing operating characteristics are that said first and second light sources are sequentially energized such that said opposed sides of the container mouth on opposite sides of the longitudinal axis of the container are alternately illuminated.

7. The apparatus set forth in claim 1 wherein said differing operating characteristics are that said first and second light sources are simultaneously energized and have differing wavelengths such that said opposed sides of the container mouth on opposite sides of the longitudinal axis of the container are illuminated by light having different wavelengths.

8. The apparatus set forth in claim 7 wherein at least first and second optical filters are operatively disposed between the container mouth and said light sensor, said filters having wavelength characteristics coordinated with the wavelength characteristics of the respective underlying light sources.

9. The apparatus set forth in claim 8, wherein said first light source transmits light of a relatively shorter wavelength, said second light source transmits light of a relatively longer wavelength, said first optical filter is a short pass filter, and said second optical filter is a long pass filter.

10. The apparatus set forth in claim 1 wherein low-angle reflections are reduced to a degree that does not interfere with image processing because said reflections are at least one of filtered before reaching said light sensor or impinge on a portion of said light sensor that is not presently evaluated.

11. The apparatus set forth in claim 1 wherein the at least first and second light sources include at least a pair of opposed light sources, wherein each light source is about 1/X in circumferentially angular size, wherein X is a quantity of images to be captured of the container.

12. The apparatus set forth in claim 1 wherein the at least first and second light sources include at least a pair of opposed light sources, wherein each light source is about 1/X in circumferentially angular size, wherein X is a quantity of portions of images to be captured of the container.

13. The apparatus set forth in claim 1 wherein each light source of the at least first and second light sources is about thirty six degrees in circumferentially angular size.

14. The apparatus set forth in claim 1 wherein said at least first and second light sources include a plurality of pairs of opposed light sources and the container is stationary as said plurality of pairs of opposed light sources are energized circumferentially sequentially around the container.

15. A method of inspecting a container having a base and a mouth, including the steps of:
directing light through the container base into the container, and out of the container through the container mouth, using at least first and second light sources operatively disposed adjacent to each other beneath the container base and having differing operating characteristics, wherein said at least first and second light sources include at least a pair of opposed light sources disposed on opposite sides of a longitudinal axis of the container, and further wherein said differing operating characteristics of said first and second opposed light sources cause different illumination amongst opposed sides of the container mouth disposed on opposite sides of the longitudinal axis of the container;
sensing light transmitted through the container mouth; and
capturing images of the container mouth in opposed pairs, each pair of images comprising images of respective segments of the container mouth disposed on opposite sides of the longitudinal axis of the container.

16. The method set forth in claim 15, including diffusing light at a location between said light source and the container.

17. The method set forth in claim 15, including focusing light at a location between the container and said light sensor.

18. The method set forth in claim 15, including rotating the container to different circumferentially angular positions for capturing additional pairs of images of the container mouth.

19. The method set forth in claim 15, including producing a composite image from said images.

20. The method set forth in claim 15 wherein said differing operating characteristics are that said first and second light sources are sequentially energized.

21. The method set forth in claim 15 wherein said differing operating characteristics are that said first and second light sources are simultaneously energized and have differing wavelengths.

22. The method set forth in claim 21 including short-pass filtering in a location between the container mouth and said light sensor to allow light from said first light source to pass, and long-pass filtering in a location adjacent to said short-pass filtering to allow light from said second light source to pass.

23. The method set forth in claim 15, wherein low-angle reflections are reduced to a degree that does not interfere with image processing because said reflections are at least one of filtered before reaching said light sensor or impinge on a portion of said light sensor that is not presently evaluated.

24. The method set forth in claim 15 wherein the at least first and second light sources include a pair of opposed light sources, wherein each light source is about 1/X in circumferentially angular size, wherein X is at least one of a quantity of images to be captured of the container or a quantity of portions of images to be captured of the container.

25. The method set forth in claim 15 wherein the at least first and second light sources include a plurality of pairs of opposed light sources, wherein each light source is about 1/X in circumferentially angular size, wherein X is at least one of a quantity of images to be captured of the container or a quantity of portions of images to be captured of the container.

26. The method set forth in claim 15 wherein said at least first and second light sources include a plurality of pairs of opposed light sources and the container is stationary as the plurality of pairs of opposed light sources are energized circumferentially sequentially around the container.

27. The method set forth in claim 15 wherein the pair of opposed light sources are diametrically opposed, and further wherein each pair of images comprises images of respective segments of the container mouth that are diametrically opposed.

28. The apparatus set forth in claim 1 wherein the pair of opposed light sources are diametrically opposed, and each pair of images comprises images of respective segments of the container mouth that are diametrically opposed.

* * * * *